United States Patent [19]

Young

[11] Patent Number: 5,067,821
[45] Date of Patent: Nov. 26, 1991

[54] DISPOSABLE BAG APPARATUS AND METHOD

[76] Inventor: J. Winslow Young, 803 E. Center St., Centerville, Utah 84014

[21] Appl. No.: 515,106

[22] Filed: Apr. 27, 1990

[51] Int. Cl.⁵ .................. B65D 30/28; B65D 33/20
[52] U.S. Cl. .......................................... 383/36; 383/44; 383/84; 383/907
[58] Field of Search .................. 383/33, 34, 36, 44, 383/48, 49, 50, 52, 57, 58, 61, 78, 80, 84, 85, 86, 87, 907, 93, 95, 904

[56] References Cited

U.S. PATENT DOCUMENTS

| | | | |
|---|---|---|---|
| 2,394,335 | 2/2946 | Shapiro | 383/84 X |
| 2,622,646 | 12/1952 | Miller | 383/93 |
| 2,804,257 | 8/1957 | Hasler et al. | 383/36 |
| 2,825,497 | 3/1958 | Hitt | 383/84 |
| 2,935,241 | 5/1960 | Brady | 383/907 X |
| 3,051,605 | 8/1962 | Stannard | 383/50 X |
| 3,172,796 | 3/1965 | Gülker | 383/907 X |
| 3,189,252 | 6/1965 | Miller | 383/57 |
| 3,282,412 | 11/1966 | Corella et al. | 383/44 X |
| 3,502,258 | 3/1970 | Kugler et al. | 383/61 X |
| 3,676,887 | 7/1972 | Klein | 383/84 X |
| 3,724,461 | 4/1973 | Eisenberg | 383/44 X |
| 3,734,154 | 5/1973 | Polk | 383/57 |
| 3,797,734 | 3/1974 | Fleury et al. | 383/36 |
| 3,920,179 | 11/1975 | Hall | 383/48 X |
| 4,182,478 | 1/1980 | Etes | 383/36 |
| 4,686,814 | 8/1987 | Yanase | 383/36 X |
| 4,758,099 | 7/1988 | Branson | 383/44 |
| 4,822,180 | 4/1989 | Gjelstrup et al. | 383/57 |
| 4,838,327 | 6/1989 | Ambler et al. | 383/36 X |
| 4,948,266 | 8/1990 | Bencic | 383/34 |
| 4,990,145 | 2/1991 | Fluery | 604/317 |

Primary Examiner—Stephen Marcus
Assistant Examiner—Jes F. Pascua
Attorney, Agent, or Firm—J. Winslow Young

[57] ABSTRACT

This invention is a disposable bag having a foldable funnel mounted in the throat of the bag. The bag has a convergent, upwardly tapered neck toward the mouth of the bag. The mouth and a portion of the neck are inverted inside the bag where it forms a reflux valve below the funnel. One side of the funnel includes an upwardly extending closure that can be folded across the funnel into sealing engagement with the other side of the funnel.

4 Claims, 2 Drawing Sheets

DISPOSABLE BAG APPARATUS AND METHOD

BACKGROUND

1. Field of the Invention

This invention relates to disposable bags and, more particularly, to a disposable bag apparatus and method wherein the open mouth at the upper end of a convergently tapered plastic bag is inverted into the plastic bag to form a reflux valve on the end of a funnel inserted into the plastic bag.

2. The Prior Art

Numerous varieties of disposable bags are used for the collection and subsequent disposal of various waste materials. These bags range from the simple plastic bag adapted to being tied off with a string, bag tie, or the like, to highly complex bag and valve systems such as that disclosed in the patent of Fleury, et al. (U.S. Pat. No. 3,797,734). The Fleury patent is directed to a funnel/bag combination wherein the funnel includes a reflux valve mounted to the lower end of the funnel. The bag is a conventional plastic bag of tubular construction with the funnel mounted in the mouth of the bag. The funnel is configured with two parallel panels that can be opened upon being squeezed from opposite edges. The valve consists of two separate sheets of plastic material suspended from each side of the funnel mouth. Liquid passing through the funnel falls into the bag between the two sheets of the valve. The sheets, being wetted by the falling liquid, tend to cling together creating a one way valve mechanism for the funnel.

Regrettably, the disposable bag of the foregoing patent is fairly complex in that it requires a number of extra parts and corresponding assembly steps thereby rendering the bag inherently more expensive for most disposable bag applications. What is needed is a simple, safe, disposable bag apparatus that is relatively inexpensive to fabricate so that it can be widely used throughout the healthcare and transportation industries. Such a novel, disposable bag apparatus and method is disclosed and claimed herein.

BRIEF SUMMARY AND OBJECTS OF THE INVENTION

This invention includes a unique combination of a flattened funnel sealingly mounted in the throat of a tapered, plastic bag. The mouth and a portion of the neck of the tapered, plastic bag are inverted into the bag where it creates a funnel extension on the lower end of the folded funnel as well as a reflux valve against accidental reflux of contents from the bag. One side of the funnel extends above the open end of the funnel to form a closure that can be folded over the flattened funnel to sealingly close both the funnel and the bag.

In view of the foregoing, it is a primary object of this invention to provide improvements in disposable bags.

Another object of this invention is to provide improvement in the method of collecting waste in a disposable bag for subsequent disposal.

Another object of this invention is to provide a novel, tapered, plastic bag wherein the mouth and a portion of the neck of the tapered, plastic bag is inverted inwardly into the bag to create a reflux valve mechanism when a funnel is sealingly engaged in the throat of the resulting plastic bag.

Another object of this invention is to provide a closure to the funnel inserted into the throat of the plastic bag.

Another object of this invention is to provide a funnel with a tapered portion that matches a portion of the taper in the throat of the tapered, plastic bag.

These and other objects and features of the present invention will become more readily apparent from the following description in which preferred and other embodiments of the invention have been set forth in conjunction with the accompanying drawing and appended claims.

DETAILED DESCRIPTION OF THE PREFERRED EMBODIMENT

Figure 1:
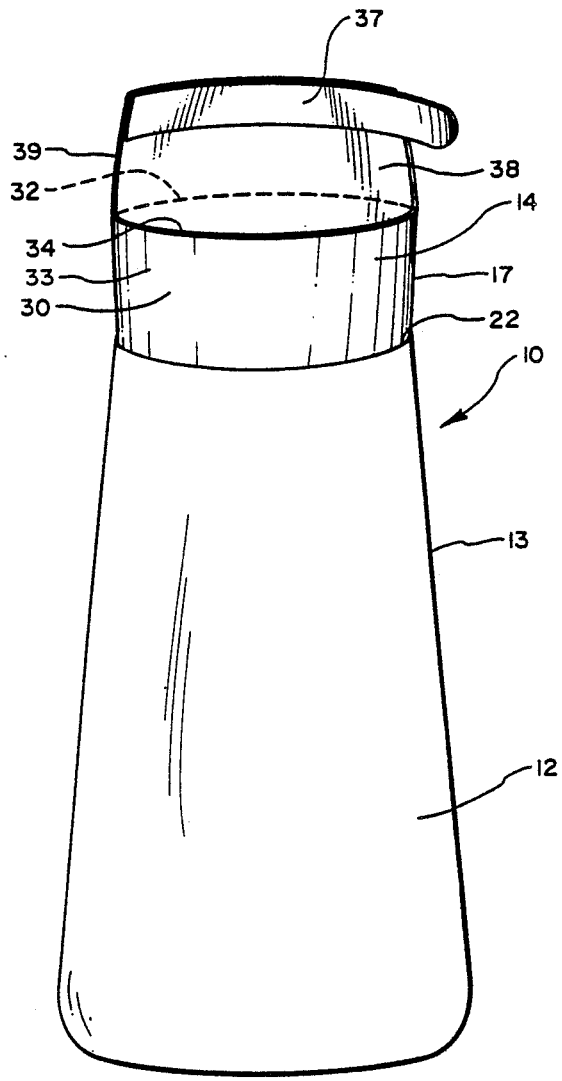
FIG. 1 is a front view of the novel, disposable bag of this invention.

The invention is best understood by reference to the drawing wherein like parts are designated by like numerals throughout in conjunction with the following description.

GENERAL DISCUSSION

The collection and subsequent disposable of human vomitus is a serious problem not only in healthcare facilities such as hospitals and nursing homes but also in all forms of transportation such as personal vehicles, trains, aircraft, ships, and the like. Historically, healthcare facilities rely on an inexpensive emesis basin that is designed as a single patient, reusable basin that is intended to be discarded when the patient is discharged. This device, though inexpensive, is designed to be flushed and cleansed after each use. Both users and nursing personnel universally dislike this conventional emesis basin because it is not only too small but also exposes to view and smell the vomitus deposited therein. Further, since these devices must be flushed and cleansed after each use there is considerable risk of secondary contamination by the contents through splashing, spillage, and the like.

The recent concern over the spread of infectious organisms via vomitus, particularly the virus responsible for the deadly disease known as AIDS (Acquired Immune Deficiency Syndrome) has resulted in extreme caution being taken in dealing with any kinds of body fluids, such as vomitus. Accordingly, there is an emerging trend to use disposable plastic bags for the collection and subsequent disposal of such products. Plastic bags are widely used for the collection of vomitus and are found readily available in aircraft, for example, for the convenience of passengers. However, a simple plastic bag must be held open with both hands rendering the user helpless in conditions of rough weather, dizziness, or the like. The foregoing disposable bag of Fleury, et al. (U.S. Pat. No. 3,797,734) clearly solves most of these problems in that it provides a funnel that permits the user to hold the bag and funnel open with only one hand.

DETAILED DESCRIPTION

Figure 2:
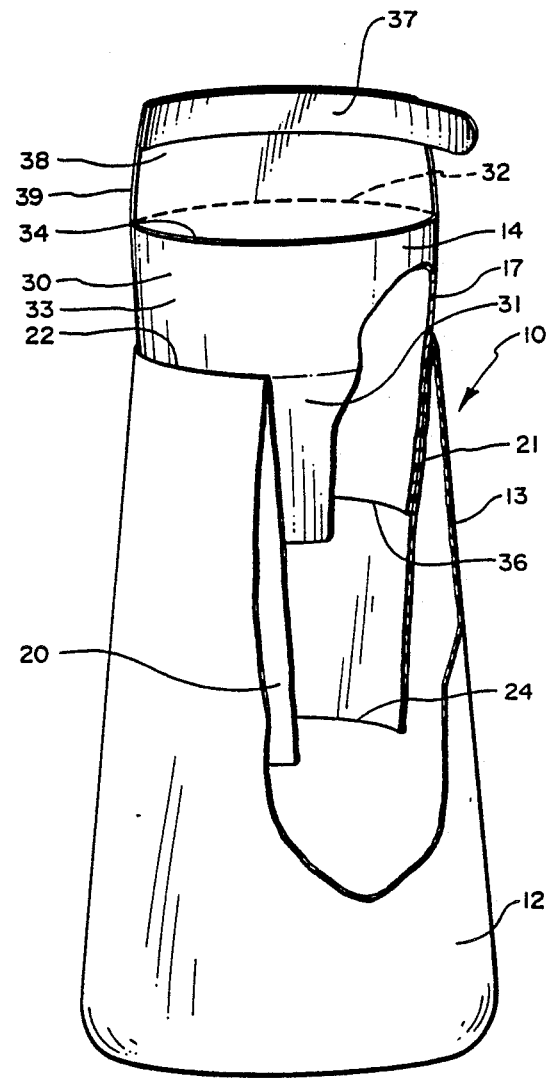
FIG. 2 is the front view of the novel, disposable bag shown in FIG. 1 with portions broken away to reveal internal features.

Referring now more particularly to FIGS. 1 and 2, the novel, disposable bag of this invention is shown generally at 10 and includes a plastic bag 12 having a tapered neck 20 (see also FIG. 3) with a partially flattened funnel 14 inserted in its throat at fold 22. Plastic bag 12 is tapered convergently in the upward direction (FIG. 3) with a slight taper 13 so that neck 20 can be inverted internally into plastic bag 12 at fold 22 to form a throat 20a (shown by broken lines) with mouth 24 becoming outlet 24a. Plastic bag 12 is elongated sufficiently to accommodate the necessary length to neck 20 so that it can be folded inwardly or otherwise inverted at fold 22.

Figure 4:
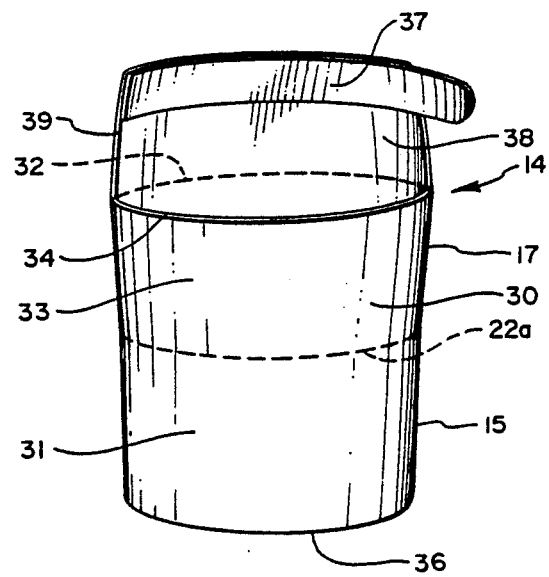
FIG. 4 is a front view of the tapered funnel that is sealingly mounted inside the throat of the plastic bag.
Figure 5:
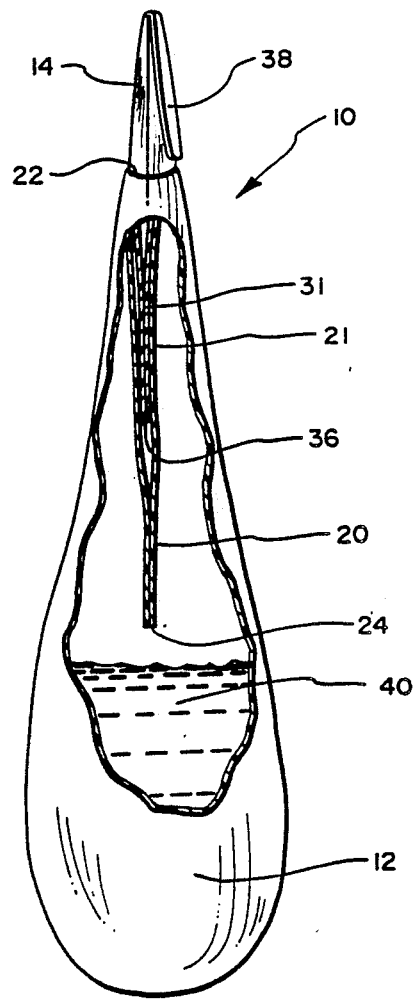
FIG. 5 is a side view of the closed, disposable bag of this invention with portions broken away to reveal internal features.

Referring now also to FIG. 4, funnel 14 is shown partially opened from its conventional flattened condition (see FIG. 5) for storage (now shown). Funnel 14 includes flattened side elements 30 between inlet 34 and an outlet 36 and has tapered sides 15 corresponding to a lower section 31 and slightly differently tapered sides 17 corresponding to an upper section 32. The change in taper between tapered sides 15 and tapered sides 17 occurs at crease 22a (shown by broken lines). The dimensions of funnel 14 at crease 22a are configured to conform with the dimensions of plastic bag 12 at fold 22. Further, the angular taper of tapered side 15 corresponds to angular taper of taper 13 of plastic bag 12 so that lower section 3 (of funnel 14 can be sealingly engaged in the throat of neck 20 (as shown in FIGS. 1, 2 and 5). The slightly outward flaring of tapered side 17 provides a convenient catchment for more securely holding funnel 14 in the hand (not shown) of user. Crease 22a also assists in the assembly of disposable bag 10 by providing a stop against which fold 22 is brought into contact during assembly.

A closure 38 is formed as an extension of one of the sidewalls of funnel 14 and is adapted to be folded at fold 32 across the open mouth 34 of funnel 14 into contact with the other side of side elements 30. An adhesive strip under overlay 37 seals closure 38 across funnel 14. Edges 39 of closure 38 are tapered inwardly in a taper that corresponds angularly with the taper of tapered sides 17.

Historically, most plastic bags are configured with a tubular construction meaning that the sidewalls are parallel along the length of the bag. Plastic bag 12 is unique in that it has a convergent taper 13 oriented upwardly toward mouth 24. When mouth 24 and the adjoining neck 20 is inverted into plastic bag 12 neck 20 becomes a funnel extension 20a (FIG. 3) that diverges away from the adjacent sidewalls to create a reflux valve mechanism. Advantageously, the reflux valve acts against the accidental reflux of contents from the interior of plastic bag 12.

With particular reference to FIG. 5, plastic bag 12 with vomitus 40 therein has been closed by funnel 14 being flattened into the flat configuration. Flap 38 has been folded downwardly over open mouth 34 along fold 32 to close the same. Overlay 37 (FIGS. 1, 2, and 4) covers a corresponding adhesive strip (not shown) on closure 38 so that the adhesive can sealingly engage the underlying portion of funnel 14. With closure 38 sealingly engaged across the open mouth 34 of funnel 14 the entire length of funnel 14 cooperates with the downwardly depending neck 20 of plastic bag 12 to provide an elongated, closed valve mechanism against the accidental reflux of vomitus 40 from plastic bag 12.

THE METHOD

Figure 3:
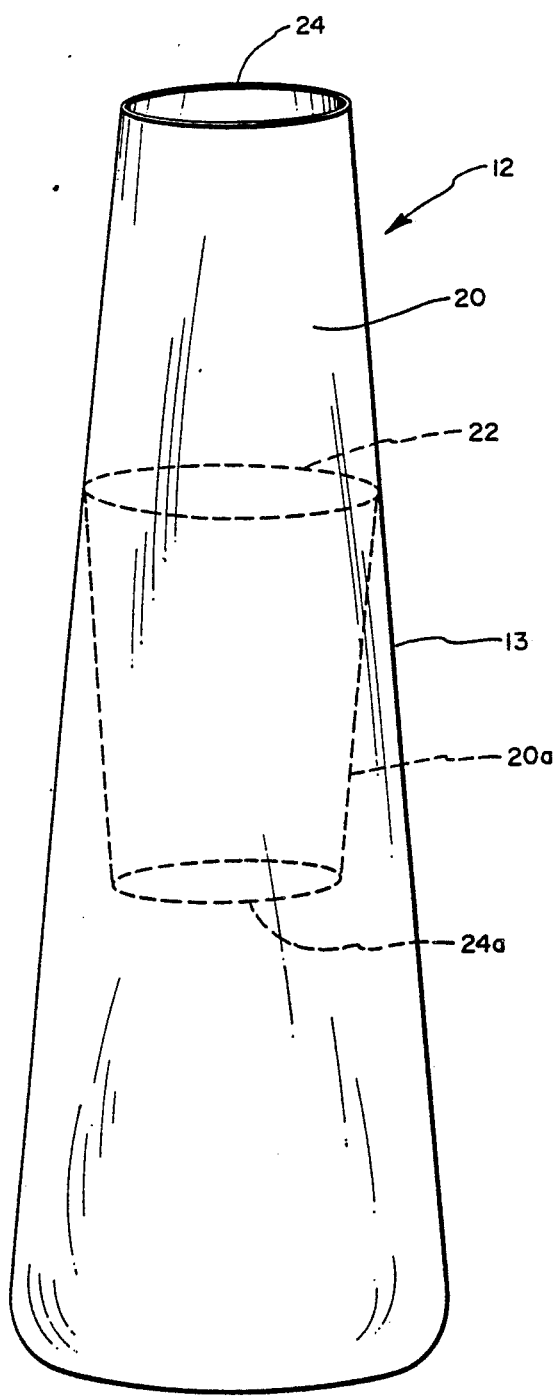
FIG. 3 is a front view of the tapered, plastic bag with a portion of the neck and mouth of the plastic bag shown schematically as being inverted inside the plastic bag (as shown by broken lines)

In practicing the method of this invention, a plastic bag 12 having tapered sidewalls 13 is fabricated into a vomitus receiving bag by inverting neck 20 inwardly into plastic bag 12 at fold 22 so that neck 20 becomes a funnel extension 20a and mouth 24 becomes an outlet 24a (FIG. 3). Funnel extension 20a thereby becomes a unidirectional valve to prevent the reflux of vomitus 40 since any reverse movement of vomitus 40 will collapse funnel extension 20a thereby preventing such reflux. A funnel for plastic bag 12 is fabricated from a suitable material such as a relatively stiff plastic or paper material such as the paper stock used for the fabrication of milk cartons, and the like. Funnel 14 is configured with a flattened configuration having tapered sidewalls 15 that match the taper of sidewalls 13. Funnel 14 is inserted into the open throat of neck 20 at fold 22. Funnel 14 will fit partway into the resulting opening with the fold 22 corresponding with the fold line 22a (FIG. 4). Adhesive is applied to section 31 on the lower end of funnel 14 so as to provide a relatively wide sealed surface between funnel 14 and plastic bag 12. A second strip of adhesive is applied to the upper end of flap 38 and covered with a removable cover 37.

With disposable bag 10 thus assembled, the downwardly depending plastic bag 12 can be folded and the entire assembly of disposable bag 10 inserted into a convenient envelope (not shown) or the like. Importantly, flap 38 is presented in an exposed manner so that it can be readily grasped and funnel 14 pulled upwardly by the user (not shown) for the rapid deployment of plastic bag 12. In particular, the user grasps funnel 14 along tapered sides 15 and, upon squeezing inwardly, outwardly deforms the two sidewalls of funnel 14 thus creating an opening having a generally oval cross section. During use, flap 38 provides a limited amount of privacy to the user (not shown) and may be quickly folded over and adhesively secured to the upper end 32 of funnel 14 thereby substantially eliminating odors and accidental reflux of vomitus 40.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced with their scope.

What is claimed and desired to be secured by United States Letters Patent is:

1. A disposable bag with an integral reflux valve and a funnel for directing liquid material through the reflux valve and into the bag, the reflux valve restricting reverse flow of liquids from the bag comprising:
   a disposable bag configured with an upwardly tapered, frustoconical configuration with an open mouth at the apex of said frustoconical configuration;
   a reflux valve inside said bag, said reflux valve being formed from an upper section of said frustoconical configuration being folded inwardly into said bag at a fold, said fold defining said upper section, said reflux valve depending downwardly into said bag at said fold; and a funnel member adhesively sealed in said reflux valve at said fold, said funnel member having an open top and an open bottom and comprising a first, flexible sidewall and a second, flexible sidewall joined along adjacent side edges, said first and second sidewalls having corresponding trapezoidal profiles with a first, long length across a top of said funnel and a second, shorter length across a bottom of said funnel, said side edges converging incrementally and downwardly toward said open mouth at an acute angle corresponding to said frustoconical configuration, said funnel being openable upon squeezing said side edges together.

2. The disposable bag defined in claim 1 wherein said first, flexible side wall of said funnel member includes a closure extending upwardly from said top and being foldable downwardly across said open top to close said first, flexible sidewall against said second, flexible sidewall, said closure including closure adhesive means for sealingly engaging said closure to said second sidewall.

3. A method for collecting a liquid in a disposable bag comprising:

preparing a disposable bag from a liquid impervious material, said bag having a closed bottom and sides with an open mouth, said sides tapering upwardly in a frustoconical configuration an upper portion of said frustoconical configuration forming a neck and converging upwardly at a first acute angle to said open mouth;

inverting said mouth and said upper portion of said frustoconical configuration inside said bag thereby forming a reflux valve in said bag, said inverting step forming a fold, said fold forming an open throat into said bag;

preparing a foldable funnel by joining two flat elements together along opposite edges thereby creating a funnel having an open top and an open bottom, said opposite edges converging downwardly at a second acute angle corresponding to said first acute angle;

mounting said funnel into said open throat with said reflux valve extending below said funnel; and depositing liquids into said bag by opening said funnel by bringing said opposite edges of said funnel together forcing said flat elements outwardly creating said funnel, said liquids passing through said funnel and said reflux valve into said bag.

4. The method defined in claim 3 wherein said preparing step includes forming a closure for said funnel by extending one of said flat elements beyond said open top, said closure being foldable across said open top.

* * * * *